United States Patent
Van der Ploeg et al.

(10) Patent No.: US 6,689,873 B1
(45) Date of Patent: Feb. 10, 2004

(54) NUCLEIC ACID ENCODING RAT AGOUTI RELATED PROTEIN

(75) Inventors: Leonardus H. T. Van der Ploeg, Scotch Plains, NJ (US); Xiaoming Guan, Edison, NJ (US); Hong Yu, Millburn, NJ (US); Prashant G. Trivedi, Monmouth Junction, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/674,320

(22) PCT Filed: Apr. 26, 1999

(86) PCT No.: PCT/US99/08983

§ 371 (c)(1), (2), (4) Date: Apr. 27, 2001

(87) PCT Pub. No.: WO99/55832

PCT Pub. Date: Apr. 11, 1999

Related U.S. Application Data

(60) Provisional application No. 60/083,549, filed on Apr. 29, 1998.

(51) Int. Cl.[7] .................. C07H 21/02; C07H 21/04; C07H 19/00; C12Q 1/68; C12P 19/34
(52) U.S. Cl. ................ 536/23.1; 435/6; 435/7.1; 435/91.1; 435/91.2; 435/320.1; 536/22.1; 536/24.3; 536/24.31; 536/24.32; 536/24.33
(58) Field of Search .................. 435/6, 7.1, 91.1, 435/91.2, 320.1; 536/22.1, 23.1, 24.3–24.33

(56) References Cited

U.S. PATENT DOCUMENTS

| | | |
|---|---|---|
| 5,766,877 A | 6/1998 | Stark et al. |
| 6,060,589 A | 5/2000 | Stark et al. |
| 6,203,995 B1 | 3/2001 | Stark |

FOREIGN PATENT DOCUMENTS

| | | |
|---|---|---|
| WO | WO97/43412 | 11/1997 |

OTHER PUBLICATIONS

Shutter, et al. "Hypothalamic expression of ART, a novel gene related to agouti, is up-regulated in obese and diabetic mutant mice". Genes & Development, vol. 11, No. 5, 1997, p. 593–602.

Graham, et al. "Overexpression of Agrt leads to obesity in trangenic mice". Nature Genetics, vol. 17, No. 3, 1997, p. 273–274.

Ollman, et al. "Antagonism of Central Melancortin Receptors in Vitro and in Vivo by Agouti–Related Protein". Science, vol. 278, 1997, p. 135–138.

Fong, et al. "Art (Protein of Agouti–Related Transcript) as an Antagonist of MC–3 and MC–4 Receptors". Biochemical and Biophysical Res. Comm: 237, 1997, p. 629–631.

*Primary Examiner*—Jeffrey Siew
(74) *Attorney, Agent, or Firm*—Jack L. Tribble; Anna L. Cocuzzo; Patricia Chisholm

(57) ABSTRACT

This invention concerns nucleic acid encoding for rat agouti related protein. Agouti related protein is a neuropeptide that may play a role in the central regulation of feeding behavior and energy metabolism via interactions with the melanocortin pathways. This invention also relates to assays utilizing the novel nucleic acid of this invention.

9 Claims, 2 Drawing Sheets cDNA sequence of rat AGRP

```
  1  CAAAGGCCAT GCTGACTGCA ATGTTGCTGA GCTGTGTCCT GCTGCTGGCA
 51  CTGCCTCCCA CATTGGGGGT CCATATGGGC GTGGCACCAC TGAAGGGCAT
101  CAGAAGGTCT GACCAGGCCC TGTTCCCAGA GTTCTCAGGT CTAAGTCTGA
151  AGAAGACAGC AGCAGACCGA GCAGAAGATG TTCTGCTGCA GAAGGCAGAA
201  GCTTTGGCAG AGGTGCTAGA TCCACAGAAC CGCGAGTCTC GTTCTCCGCG
251  TCGCTGTGTA AGGCTGCACG AGTCCTGCTT GGGACAACAG GTACCTTGCT
301  GCGACCTCTC CGCCACGTGC TACTGCCGCT TCTTCAATAC CTTTTGCTAC
351  TGCCGCAAGC TAGGTACTGG CACCACGAAC CTCTGCAGCC GCCCCTAGCC
401  AACGGATGTT GGGCAAAGGC AGGGGACGCG AATAAACGAT GGGACTAACT
451  CTAAAAAAAA AAAAAAAAAA
```

FIG. 1

Protein sequence of rat AGRP

```
  1  MLTAMLLSCV LLLALPPTLG VHMGVAPLKG IRRSDQALFP EFSGLSLKKT
 51  AADRAEDVLL QKAEALAEVL DPQNRESRSP RRCVRLHESC LGQQVPCCDL
101  CATCYCRFFN TFCYCRKLGT GTTNLCSRP*
```

FIG.2

NUCLEIC ACID ENCODING RAT AGOUTI RELATED PROTEIN

This application claims the benefit of Provisional application Ser. No. 60/083,549, filed Apr. 29, 1998.

FIELD OF THE INVENTION

This invention relates to nucleic acids encoding for rat agouti related protein. Agouti related protein is a neuropeptide that may play a role in the central regulation of feeding behavior and energy metabolism via interactions with the melanocortin pathways.

BACKGROUND OF THE INVENTION

While normally related to the production of black or yellow pigment in the hair, ubiquitous expression of agouti protein has been implicated in the occurrence of obesity and diabetes in yellow obese mice. Agouti related protein (AGRP; also known as ART and AGRT), a recently identified neuropeptide, shares some sequence homology with agouti protein and may play a role in the central regulation of feeding behavior and energy metabolism via interactions with the melanocortin pathways in a manner similar to agouti protein. When tested to see whether this homolog caused the onset of the same symptoms, it was observed that the overexpression of AGRT correlated with weight gain; see Graham et al., 1997 Nature Genetics 17:273–274 and Ollmann et al., 1997 Science 278:135–138. Moreover, AGRP mRNA is up-regulated in leptin-function deficient animals such as ob/ob and db/db mice (Shutter et al., Genes Dev. 11, 593,602, 1997).

The DNA sequence of AGRP has been reported for human and mouse; Shutter et al., 1997 Genes Dev. 11:593–602, Ollmann et al., 1997 Science 278:135–138. The human gene for ART is a 132-amino acid protein that is 25% identical to human agouti protein and is expressed primarily in the adrenal gland, subthalamic nucleus, and hypothalamus with a lower level of expression occurring in testis, lung, and kidney. The murine homolog of ART encodes a 131-amino acid protein that shares 81% amino acid identity to human ART with localized expression in the arcuate nucleus of the hypothalamus, the median eminence, and the adrenal medulla.

Attempts at detecting in situ hybridization signals of AGRP mRNA in rat brain with probes based on mouse AGRP sequences have proved unsuccessful. Since the rat is the primary animal model in the field of feeding regulation research, it is critical to characterize the function of AGRP in rats with the AGRP sequence from the same species. It is, thus, an object of the present invention to provide a compound that can recapitulate these same symptoms in rats so as to further our current knowledge in the field of feeding regulation. Such a compound could be used for developing tools to characterize the biological function of this neuropeptide, and to discover new drugs which modulate AGRP and melanocortin functions.

SUMMARY OF THE INVENTION

This invention relates to isolated nucleic acids encoding rat agouti related protein. Preferred embodiments include nucleic acid of the sequence set forth in SEQ ID NO:1 and nucleic acids which are complementary to it. This invention also relates to the protein encoded thereby (rat AGRP), vectors comprising said nucleic acid, and host cells comprising said vectors. Lastly, the present invention relates to processes utilizing the nucleic acids or protein of the present invention, such as the generation of antibodies to rat AGRP through the injection of fragments or full length rat AGRP into rabbits and recovery of the antibodies therefrom.

BRIEF DESCRIPTION OF THE DRAWINGS

FIG. 1 depicts the DNA sequence of rat AGRP (SEQ ID NO:1).

FIG. 2 depicts the amino acid sequence of rat AGRP (SEQ ID NO:2).

DETAILED DESCRIPTION OF THE INVENTION

As used throughout the specification and claims, the following definitions apply:

"AGRP" means agouti related protein. Throughout the specification, AGRP, ART and AGRT are referred to interchangeably.

"ART" or "AGRT" means agouti related transcript. This term is used to describe a nucleic acid molecule or fragment thereof that (a) comprises the nucleotide sequence as set forth in SEQ ID NO:1; (b) comprises a nucleic acid sequence encoding a polypeptide that is at least 70 percent identical, preferably at least 80 percent identical and most preferably at least 90 percent identical to the polypeptide encoded by SEQ ID NO:1; (c) is a naturally occurring allelic variant of (a) or (b); (d) is a nucleic acid variant of (a)–(c); and/or (e) is complementary to (a)–(d).

"ART protein" or "ART polypeptide" or "rat AGRP" as used herein refers to any protein or polypeptide having the properties characteristic of ART (i.e., the capability of modulating the signaling activity of a melanocortin receptor, the capability of modulating intracellular cyclic AMP (cAMP) levels, and/or the capability of modulating lipid metabolism). The ART polypeptide may or may not have an amino terminal methionine. By way of illustration, ART protein or ART polypeptide includes an amino acid sequence encoded by the nucleic acid molecule set forth in any of items (a) or (e) above and peptide or polypeptide fragments derived therefrom, the amino acid sequence set forth in SEQ ID NO:2 and/or chemically modified derivatives as well as nucleic acid and/or amino acid sequence variants thereof.

"ART fragment" or "fragment of agouti-related protein" refers to a peptide or polypeptide that is less than the full length amino acid sequence of naturally occurring ART protein but has substantially the same biological activity as ART polypeptide or ART protein described above. Such a fragment may be truncated at the amino terminus, the carboxy terminus, and/or internally, and may be chemically modified. Preferably, the ART fragment will be a carboxy terminal fragment which retains at least all 10 C-terminal cysteine residues. Such ART fragments may be prepared with or without an amino terminal methionine.

"ART derivative" or "ART variant" refers to an ART polypeptide or ART protein that has 1) been chemically modified, as for example, by addition of polyethylene glycol or other compound, and/or 2) contains one or more nucleic acid or amino acid sequence substitutions, deletions, and/or insertions.

"Biologically active polypeptide" and "biologically active fragment" refer to a peptide or polypeptide that has ART activity (i.e., is capable of modulating the signaling activity of a melanocortin receptor, is capable of modulating intracellular cAMP levels, and/or is capable of modulating lipid metabolism).

"Stringent conditions" means approximately 35° C. to 65° C. in a salt solution of approximately 0.9 molar NaCl. Stringency may also be governed by such reaction parameters as the concentration and type of ionic species present in the hybridization solution, the types and concentrations of denaturing agents present, and the temperature of hybridization. Generally as hybridization conditions become more stringent, longer probes are preferred if stable hybrids are to be formed. As a rule, the stringency of the conditions under which a hybridization is to take place will dictate certain characteristics of the preferred probes to be employed. Such relationships are well understood and can be readily manipulated by those skilled in the art.

The present invention relates to newly identified nucleic acids encoding rat agouti related protein (AGRP), and more preferably nucleic acid comprising the sequence set forth in SEQ ID NO:1. In comparison to the human and mouse AGRP, the rat sequence exhibits marked diversity including most significantly a deletion of 4 and 3 amino acid residues, respectively, in the N-terminal region. This structural difference between species may explain failed attempts to detect in situ hybridization signals of AGRP mRNA in rat brain by using probes based on mouse AGRP sequences. The present invention also relates to isolated rat AGRP and, more preferably, rat AGRP comprising the sequence set forth in SEQ ID NO:2.

Nucleic acid in accordance with the present invention, and preferably cDNA, can be isolated by methods well known in the art including, without limitation, polymerase chain reaction (PCR), as well as cDNA and/or genomic library screening with suitable probes (usually oligonucleotides and/or antibodies for cDNA libraries, and oligonucleotides or cDNA sequences for genomic libraries). Some of these methods as well as other methods useful for molecular cloning are set forth by Sambrook et al., *Molecular Cloning: A Laboratory Manual*, Cold Spring Harbor Laboratory Press, Cold Spring Harbor, N.Y. (1989). The nucleic acid may be any nucleic acid which can encode a protein such as genomic DNA, cDNA or any of the various forms of RNA.

Polypeptides constitute yet another aspect of the invention and may be naturally occurring full length polypeptides, or truncated polypeptides or peptides (i.e., "fragments"). The polypeptides or fragments may be chemically modified, i.e., glycosylated, phosphorylated, and/or linked to a polymer and they may have an amino terminal methionine. In addition, the polypeptides or fragments may be variants of the naturally occurring ART polypeptide (i.e., may contain one or more amino acid deletions, insertions, and/or substitutions as compared with naturally occurring ART). The polypeptide of FIG. 2 is 129 amino acids long with an open reading frame of 387 basepairs, and exhibits 93.8% homology to mouse AGRP at the amino acid level and 78.3% homology to human AGRP at the amino acid level.

The full length AGRP polypeptide or fragment thereof can be prepared using well known recombinant DNA technology methods such as those set forth in Sambrook et al., supra, and/or Ausubel et al., eds., *Current Protocols in Molecular Biology*, Green Publishers Inc. and Wiley and Sons, NY (1994). A gene or cDNA encodingithe ART protein or fragment thereof may be obtained for example by screening a genomic or cDNA library, or by PCR amplification. Alternatively, a gene encoding the ART polypeptide or fragment may be prepared by chemical synthesis using methods well known to the skilled artisan such as those described by Engels et al., 1989 *Angew. Chem. Intl. Ed.* 28:716–734. These methods include, inter alia, the phosphotriester, phosphoramidite, and H-phosphonate methods for nucleic acid synthesis. A preferred method for such chemical synthesis is polymer-supported synthesis using standard phosphoramidite chemistry.

Typically, the DNA encoding the ART polypeptide will be several hundred nucleotides in length. The cDNA of FIG. 1 is 470 basepairs in length, exhibiting 94.6% homology to mouse AGRP at the nucleotide level and 82.9% homology to human AGRP at the nucleotide level. Nucleic acids larger than about 100 nucleotides can be synthesized as several fragments using these methods. The fragments can then be ligated together to form the full length ART polypeptide. Usually, the DNA fragment encoding the amino terminus of the polypeptide will have an ATG, which encodes a methionine residue. This methionine may or may not be present on the mature form of the ART polypeptide, depending on whether the polypeptide produced in the host cell is secreted from that cell.

Nucleic acid and/or amino acid variants of naturally occurring ART are also encompassed within the scope of this invention. Nucleic acid variants (wherein one or more nucleotides differ from the wild-type or naturally occurring ART) may be produced using site directed mutagenesis or PCR amplification where the primer(s) have desired point mutations; see Sambrook et al., supra, and Ausubel et al., supra, for descriptions of mutagenesis techniques. Chemical synthesis using methods described by Engels et al., sura, may also be used to prepare such variants. Other methods known to the skilled artisan may be used as well.

The ART gene or cDNA can be inserted into an appropriate expression vector for expression in a host cell; such vector comprising the nucleic acid of the instant invention constituting one further aspect of the invention. The vector may be any known vector, including plasmids, cosmids and viral vectors which can function in a chosen host cell. Preferred vectors for practicing this invention are those which are compatible with bacterial, insect, and mammalian host cells. Such vectors include, inter alia, pcDNA3 (Invitrogen Company, San Diego, Calif.), pBluescriptII (Stratagene Company, LaJolla, Calif.), and BlueBacII (Invitrogen). The vector utilized should be selected to be functional in the particular host cell employed (i.e., the vector is compatible with the host cell machinery such that amplification of the ART gene and/or expression of the gene can occur). The AGRP polypeptide or fragment thereof may be amplified/expressed in prokaryotic (such as *E. coli*) or eukaryotic (including yeast, insect and mammalian) host cells.

Typically, the vectors used in any of the host cells will contain a 5' flanking sequence (also referred to as a "promoter"), whether it be a native (i.e., from the same species and/or strain as the host cell), heterologous (i.e., from a different species and/or strain), or a hybrid thereof. Optionally, the vectors may also contain other expression-control elements, such as enhancers and sequences which assist the host in expressing the peptide, such as an origin of replication element, a transcriptional termination element, a complete intron sequence containing a donor and acceptor splice site, a signal peptide sequence, a ribosome binding site element, a polyadenylation sequence, a polylinker region for inserting the nucleic acid encoding the polypeptide to be expressed, and/or a selectable marker element. Where such elements are not already present in the vector to be used, they may be individually obtained and ligated into the vector. Methods used for obtaining these elements are well known to the artisan of ordinary skill in the art.

The nucleic acid may then be transfected into a selected cell line for expression and evaluation; the host having been transfected with a vector of the instant invention constituting another aspect of the present invention. Transfection can be accomplished using any known method, including without limitation, the calcium phosphate procedure, electroporation, viral infection (e.g., via the use of retroviruses), lipofection, DEAE-dextran, or microinjection. The transfection method used will depend in part on the cell type being transfected. For bacterial cells, electroporation is generally preferred. For mammalian cells, transfection can be accomplished using electroporation, or alternatively, the DEAE-dextran method as described in Section 9.2 of Ausubel et al., *Current Protocols in Molecular Biology*, 1987.

The host cell may be any cell or cell line which is conveniently cultured. In general, a preferred host cell will be eukaryotic, preferably mammalian and, most preferably, selected from the group consisting of Chinese Hamster Ovary cells, HeLa cells, COS-1 and COS-7 monkey cells, melanoma cell lines (such as, Bowes cells), mouse L-929 cells, 3T3 lines derived from Swiss, Balb-c or NIH mice, BHK or HaK hamster cell lines, and the CV-1 cell line. Normal diploid cells, cell strains derived from in vitro culture of primary tissue, as well as primary explants (including relatively undifferentiated cells such as hematopoietic stem cells) are also suitable.

Other suitable host cells are prokaryotic cells, such as bacterial cells (in particular, the various strains of *E. coli*, for example HB101, DH5α, DH10, and MC1061).

Many strains of yeast cells known to those skilled in the art are also available as host cells for expression of the polypeptides of the present invention. Additionally, where desired, insect cells may be utilized as host cells in the method of the present invention.

The host cell, when cultured under appropriate conditions, can synthesize AGRP protein which can subsequently be collected from the culture medium (if the host cell secretes it into the medium) or directly from the host cell producing it (if it is not secreted). After collection, the AGRP protein can be purified using methods such as molecular sieve chromatography, affinity chromatography, and the like.

The present invention, thus, includes a process for producing rat agouti related protein comprising constructing a vector comprising the nucleic acid of the present invention, transforming a host cell with said vector, culturing said transformed cell and recovering said protein from the culture.

The present invention also includes a process for producing anti-rat agouti related protein antibodies wherein (i) the full length agouti related protein or fragment thereof is injected into a rabbit or other animal recognized as optimal for generating antibodies and (ii) antibodies specific for rat AGRP are recovered. Methods in accordance with this aspect of the invention are well known to one lof ordinary skill in the art.

The following non-limiting Examples are presented to better illustrate the present invention.

EXAMPLE 1

RNA Preparation

Nine fatty Zucker rats (male, 600–800 grams, 6 months old) were decapitated under carbon dioxide ($CO_2$) anesthesia. The hypothalami were quickly removed and frozen in liquid nitrogen. Total RNA was prepared from the hypothalamic tissues using the ULTRSPEC™ RNA isolation kit (Biotecx Laboratories, Inc., Houston, Tex.) following the manufacturer's protocol.

EXAMPLE 2

RT-PCR

A cDNA template for PCR reactions was synthesized using 1 µg of the rat hypothalamic RNA and both random and oligo DT priming with the advantage RT-FOR-PCR kit (clontech, palo alto, Calif.), following the manufacturer's protocol. The first round of PCR was carried out by mixing 2 µl 10 mm DNTP, 10 µl 10×PCR buffer, 4 µl 50 mm $MgCl_2$, 10 µl of reverse transcribed cDNA (an equal mixture of random and oligo DT primed products), and 5 µl each of 20 mm PCR primer #290 (5'-TAGATGGATCCATGCTGACCGCAATG-3': SEQ ID NO:3) and #291 (5'-AGTCAGAATTCTAGGTGCGGCTGCA-3'; SEQ ID NO:4), and deionized water to a total volume of 100 µl. After being heated at 95° C. for 5 min., The sample tube was placed on ice, then 2.5 u of TAQ polymerase was added to the tube followed by the addition of 50 µl of mineral oil. The PCR conditions were as follows: 94° C.×1 min. Followed by an annealing step of 42° C.×1.5 min., Followed by 72° C.×2 min., And the whole cycle was repeated 20 times. The second round (nested) PCR was carried out by mixing 2 µl 10 mm DNTP, 10 µl 10×PCR buffer, 4 µl 50 mm $MgCl_2$, 1 µl of first round PCR product (as template), and 5 µl each of 20 mm PCR primer #292(5'-CTGGCACTGCCTGCCAC-3'; SEQ ID NO:5) and #294 (5'-GCACATGGGTCACAGCA-3': SEO ID NO:6), and deionized water to a total volume of 100 µl. The cycling conditions were the same as the first round PCR except that annealing temperature was changed to 45° C. and the cycles were repeated 25 time. The PCR product of about 200 bp was purified with QIAQUICK PCR purification kit (Qiagen, Valencia, Calif.), and verified to be rat AGRP by DNA sequencing.

EXAMPLE 3

Screening of cDNA Library

The above-mentioned 200 bp PCR products of rat AGRP were purified on a 1% agarose gel followed by Qiaex II Kit (Qiagen, Valencia, Calif.) and labeled by random-priming with [α-$^{32}$P] dCTP using Redi-Prime kit (Amersham, Arlington Heights, Ill.) to a specific activity of 2×10$^8$ dpm/µg DNA. This radiolabeled probe was used to screen a cDNA library of rat hypothalamus (Howard et al., FEBS Lett. 405, 285–290, 1997). The library (about 700,000 cfu) was plated onto LB/ampicillin plates overlaid with nylon filters. After overnight growing at 37° C., the replica filters were made, processed and hybridized at 42° C. for 18 hours in 6×SSC buffer containing 50% formamide, 5×Denhardt's solution, 0.1% SDS, 20 µg/ml sheared salmon-sperm DNA with the 2×10$^6$ cpm/ml $^{32}$P-labeled probes. The filters were washed in 0.1×SSC, 0.1% SDS at 65° C., and exposed to X-ray films for 48 hours. Two independent clones were identified. DNA was prepared from these clones using WIZARD miniprep kit (Promega, Madison, Wis.), and subjected to semi-automated sequence analysis using the PRISM Dye Deoxy terminator cycle sequencing kit (Applied Biosystems, Foster City, Calif.) on an ABI 377 sequencer.

What is claimed is:

1. An isolated nucleic acid comprising a nucleotide sequence which encodes a rat agouti polypeptide wherein said nucleic acid comprises the nucleotide sequence set forth in SEQ ID NO: 1.

2. The nucleic acid in accordance with claim 1, which is cDNA.

3. A vector comprising the nucleic acid of claim 1.

4. A vector according to claim 3 which is a viral vector.

5. A host cell comprising a vector in accordance with claim 3.

6. A host cell according to claim 5 which is a mammalian cell.

7. A host cell according to claim 5 which is *E. coli.*

8. A process for producing rat agouti related protein comprising constructing a vector comprising the nucleic acid of claim 1, transforming a host cell with said vector, culturing said transformed cell and recovering said protein.

9. The process of claim 8 wherein the host cell is a eukaryotic cell.

* * * * *

SEQUENCE LISTING

<160> NUMBER OF SEQ ID NOS: 6

<210> SEQ ID NO 1
<211> LENGTH: 470
<212> TYPE: DNA
<213> ORGANISM: rattus norvegicus

<400> SEQUENCE: 1
caaaggccat gctgactgca atgttgctga gctgtgtcct gctgctggca ctgcctccca       60
cattgggggt ccatatgggc gtggcaccac tgaagggcat cagaaggtct gaccaggccc      120
tgttcccaga gttctcaggt ctaagtctga agaagacagc agcagaccga gcagaagatg      180
ttctgctgca gaaggcagaa gctttggcag aggtgctaga tccacagaac cgcgagtctc      240
gttctccgcg tcgctgtgta aggctgcacg agtcctgctt gggacaacag gtaccttgct      300
gcgacctgtg cgccacgtgc tactgccgct tcttcaatac cttttgctac tgccgcaagc      360
taggtactgg caccacgaac ctctgcagcc gcccctagcc aacggatgtt gggcaaaggc      420
aggggacgcg aataaacgat gggactaact ctaaaaaaaa aaaaaaaaa                  470

<210> SEQ ID NO 2
<211> LENGTH: 129
<212> TYPE: PRT
<213> ORGANISM: rattus norvegicus

<400> SEQUENCE: 2

Met Leu Thr Ala Met Leu Leu Ser Cys Val Leu Leu Ala Leu Pro
 1               5                  10                  15

Pro Thr Leu Gly Val His Met Gly Val Ala Pro Leu Lys Gly Ile Arg
             20                  25                  30

Arg Ser Asp Gln Ala Leu Phe Pro Glu Phe Ser Gly Leu Ser Leu Lys
         35                  40                  45

Lys Thr Ala Ala Asp Arg Ala Glu Asp Val Leu Leu Gln Lys Ala Glu
     50                  55                  60

Ala Leu Ala Glu Val Leu Asp Pro Gln Asn Arg Glu Ser Arg Ser Pro
65                  70                  75                  80

Arg Arg Cys Val Arg Leu His Glu Ser Cys Leu Gly Gln Gln Val Pro
                 85                  90                  95

Cys Cys Asp Leu Cys Ala Thr Cys Tyr Cys Arg Phe Phe Asn Thr Phe
            100                 105                 110

Cys Tyr Cys Arg Lys Leu Gly Thr Gly Thr Thr Asn Leu Cys Ser Arg
        115                 120                 125

Pro

<210> SEQ ID NO 3
<211> LENGTH: 26
<212> TYPE: DNA
<213> ORGANISM: Artificial Sequence
<220> FEATURE:
<223> OTHER INFORMATION: PCR primer

<400> SEQUENCE: 3
tagatggatc catgctgacc gcaatg                                            26

<210> SEQ ID NO 4
<211> LENGTH: 25
<212> TYPE: DNA
<213> ORGANISM: Artificial Sequence -continued

```
<220> FEATURE:
<223> OTHER INFORMATION: PCR primer

<400> SEQUENCE: 4
agtcagaatt ctaggtgcgg ctgca                                              25

<210> SEQ ID NO 5
<211> LENGTH: 17
<212> TYPE: DNA
<213> ORGANISM: Artificial Sequence
<220> FEATURE:
<223> OTHER INFORMATION: PCR primer

<400> SEQUENCE: 5
ctggcactgc ctgccac                                                       17

<210> SEQ ID NO 6
<211> LENGTH: 17
<212> TYPE: DNA
<213> ORGANISM: Artificial Sequence
<220> FEATURE:
<223> OTHER INFORMATION: PCR primer

<400> SEQUENCE: 6
gcacatgggt cacagca                                                       17
```